(12) United States Patent
Dib

(10) Patent No.: US 6,339,095 B2
(45) Date of Patent: *Jan. 15, 2002

(54) THERAPEUTIC USE OF 1, 6-DIMETHYL-8β-HYDROXYMETHYL-10-α-METHOXYERGOLINE

(75) Inventor: Michel Dib, Paris (FR)

(73) Assignee: Aventis Pharma S.A., Antony Cedex (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/863,610

(22) Filed: May 23, 2001

Related U.S. Application Data

(63) Continuation of application No. PCT/FR99/02868, filed on Nov. 22, 1999.

(30) Foreign Application Priority Data

Nov. 13, 1998 (FR) .............................. 98 14250

(51) Int. Cl.⁷ .............................. H61K 31/445
(52) U.S. Cl. ...................................... 514/323
(58) Field of Search ......................... 514/323

(56) References Cited

U.S. PATENT DOCUMENTS 4,232,157 A * 11/1980 Enrico
4,908,449 A * 3/1990 Gervais
4,980,475 A * 12/1990 Bombardelli et al.

FOREIGN PATENT DOCUMENTS

| BE | 633438 | | 11/1963 |
| DE | 4240798 | * | 6/1993 |
| EP | 0004664 | | 4/1979 |
| FR | 2616788 | | 6/1987 |

OTHER PUBLICATIONS

Shintomi et al., Pharmacological effects of nicergoline and its metabolites . . . , abstract, J. Pharmacobio–Dyn., 1987, vol. 10(1), pp. 35–48.*

Moretti et al., Effect of ergoline on neurotransmitter system . . . , abstract, Arch. Int. Pharmacodyn. 1988, vol. 294, pp. 33–45.*

Schnaar, R.L., et al: *The Journal of Neuroscience*, vol. 1 (2) pp. 204–217 (1981).

Arcamone, F., et al: *Biochemical Pharmacology*, vol. 21 (16) pp. 2205–2213 (1972).

Estevez, A.G., et al: *Journal of Neuroscience*, vol. 18 (3) pp. 923–931 (1998).

Camu, W., et al: *Journal of Neuroscience Methods*, vol. 44, pp. 59–70 (1992).

* cited by examiner

Primary Examiner—William R. A. Jarvis
Assistant Examiner—Vickie Kim
(74) Attorney, Agent, or Firm—Balaram Gupta

(57) ABSTRACT

The invention concerns the use of 1,6-dimethyl-8β-hydroxymethyl-10α-methoxyergoline for preventing and/or treating motor neuron diseases.

6 Claims, No Drawings

THERAPEUTIC USE OF 1, 6-DIMETHYL-8β-HYDROXYMETHYL-10-α-METHOXYERGOLINE

This application is a continuation of International application No. PCT/FR99/02868, filed Nov. 22, 1999; which claims the benefit of priority of French Patent Application No. 98/14,792, filed Nov. 24, 1998.

The present invention relates to the use of 1,6-dimethyl-8β-hydroxymethyl-10α-methoxyergoline in the prevention and/or treatment of motor neuron diseases.

1,6-Dimethyl-8β-hydroxymethyl-10α-methoxy-ergoline or 1-methyl-10α-methoxy-9,10-dihydrolysergol is one of the metabolites of nicergoline (F. ARCAMONE et al., Biochem. Pharmacol., 21 (16), 2205–2013 (1972)). Like nicergoline, but to a lesser degree, this compound exhibits α1-adrenergic and 5HT1a-serotonergic properties. It is also useful as an intermediate for preparing nicergoline (French Patent No. 2,616,788).

It has now been found that 1,6-dimethyl-8β-hydroxymethyl-10α-methoxyergoline increases the survival of motor neurons and can therefore be used in preventing and/or treating motor neuron diseases.

Motor neuron diseases include, in particular, amyotrophic lateral sclerosis, progressive spinal muscular atrophy, infantile muscular atrophy and primary lateral sclerosis.

In the presence of trophic support supplied by the neurotrophic factors BDNF or GDNF, motor neuron cultures are composed of broad and homogeneous neurons with long branched axons. However, the motor neurons die by apoptosis if the culture is performed in the absence of trophic support.

The effect of 1,6-dimethyl-8β-hydroxymethyl-10α-methoxyergoline has therefore been determined in a degeneration model which is induced by depriving cultured motor neurons of neurotrophic factor.

Furthermore, astrocytes play a major role in controlling and maintaining an environment which is suitable for motor neuron survival.

1,6-Dimethyl-8β-hydroxymethyl-10α-methoxyergoline has therefore also been tested on a co-culture of motor neurons and astrocytes.

The following protocols were employed:

MOTOR-NEURON-ENRICHED CULTURES:

The motor-neuron-enriched cultures are prepared using the centrifugation method which was described by R. L. SCHNAAR and A. E. SCHAFFNER, J. Neurosci., 1, 204–217 (1981) and modified by W. CAMU and C. E. HENDERSON, J. Neurosci. Methods, 44, 59–70 (1992). The motor neurons are spread, at a density of 2500 cells per plate, on 35 mm culture plates which have previously been coated with laminin/ornithine in accordance with the method of A. G. ESTEVEZ et al., J. Neurosci., 18 (3), 923–931 (1998). The cultures are then maintained in L15 medium (GIBCO BRL) containing sodium bicarbonate (22 mM), conalbumin (0.1 mg/ml), putrescine (0.1 mM), insulin (5 µg/ml), sodium selenite (31 mM), glucose (20 mM), progesterone (21 nM), penicillin (100 IU/ml) and streptomycin (100 µ/ml).

The motor neurons which are thus obtained consist of large (25–30 µm) and homogeneous neurons which possess long branched axons. More than 70% of the cells are immunoreactive for the neurotrophin p75 receptor and the Islet ½ markers for spinal motor neurons. Approximately 70% of the motor neurons die by apoptosis 24 hours after the spreading if the culture is performed in the absence of a trophic factor.

CULTURES OF SPINAL CORD ASTROCYTES:

The astrocytes are obtained from young, one-day-old rats using the slightly modified method of R. P. SANETO and J. DE VELLIS as described in Neurochemistry a practical approach (A. J. TURNER and H. A. St JOHN) IRL Press, Oxford-Washington DC, pp. 27–63. The spinal cords are dissected out under sterile conditions and freed of meninges and dorsal ganglia. Five to ten spinal cords are transferred into PBS (phosphate buffered saline) and cut before being incubated at 37° C. for 25 minutes in PBS to which 0.25% trypsin has been added. The enzymatic treatment is stopped by adding 10 ml of Dulbeccols modified Eagle medium (DMEM), to which 10% fetal calf serum (FCS) has been added, and the cells are collected by centrifugation. Another step of mechanical dissociation is performed using the end of a 1 ml pipette. The cells are spread, at a density of 1.5–2×10$^6$ cells per 25 cm$^2$ of culture medium, in DMEM containing 10% FCS. After 2 days in vitro, the cultures are fed every day. When a visible monolayer of cells has been completed, the cultures are stirred at 250 rpm for 48 hours and, on the following day, the monolayers are treated with cytosine arabinoside (10$^{-5}$ M) for 48 hours. The astrocyte monolayers are then amplified to a density of five on 35 mm culture plates for initially 25 cm$^2$ culture flasks.

The spinal astrocyte cultures consist, to an extent of more than 98%, of flat, polygonal cells which are immunoreactive for the glial fibrillar acid protein (GFAP). The monolayers are exposed to the product to be tested and then incubated with the motor neuron medium in order to obtain a conditioned culture medium. This medium is transferred and tested at different dilutions in order to determine its effects on neuronal survival.

IMMUNOCHEMISTRY

The cells are fixed in 4% paraformaldehyde and 0.1% glutaraldehyde in PBS (pH 7.4 and at 4° C. for 15 minutes) and in a cold methanolic solution. The cultures are then washed and the nonspecific sites are blocked with 10% goat serum and 2% bovine serum albumin (BSA) in PBS and treated for immunochemistry using antibodies against the p75 weak affinity neurotrophin receptor or a 200 kD neurofilament protein (Amersham) using the manufacturer's instructions and applying the avidin-biotin-DAB/hydrogen peroxide enhancement reaction.

TREATING THE ASTROCYTES WITH 1,6-DIMETHYL-8β-HYDROXYMETHYL-10α-METHOXYERGOLINE

The astrocytes are treated with 1,6-dimethyl-80β-hydroxymethyl-10α-methoxyergoline in the following manner: the product is dissolved in methanol, sterilized by filtration and used immediately after preparation. The treatment which is applied to the enriched motor neuron cultures is effected by adding aliquots of solutions of the products to be tested to the L15 medium by spreading. The astrocyte monolayers are exposed to the vehicle or to the solutions of the compound to be tested for 24 hours and at different concentrations. The astrocyte monolayers are washed 3 times with DMEM and incubated with complete L15 medium. he astrocyte-conditioned medium is recovered 24 hours later and centrifuged at 1800 g for 15 minutes and used immediately or stored at–70° C. for a maximum of 2 weeks without loss of trophic activity.

COUNTING THE CELLS AND STATISTICAL ANALYSIS

The cells which are immunoreactive for neurofilaments and which exhibit axons which are longer than the diameters of the cells are regarded as being viable motor neurons. The number of motor neurons is estimated by counting the labelled cells in an area of 0.4–1 cm² under a microscope which enlarges 200 times. In all cases, the values are expressed as a percentage of the number of motor neurons which are present in cultures maintained using trophic factors. The experiments are carried out at least 3 times.

The statistical analyses are performed using the Student's test (t test).

The following results were obtained:

1—Effect of 1,6-dimethyl-8β-hydroxymethyl-10α-methoxyergoline on neuronal survival in astrocyte/motor neuron co-cultures:

|  | % of labelled motor neurons | |
| --- | --- | --- |
|  | All the motor neurons | Very large motor neurons |
| Vehicle alone | 100 ± 9.4 | 100 ± 2.8 |
| 1,6-Dimethyl-8β-hydroxymethyl-10α-methoxyergoline | | |
| 0.1 μM | 123 ± 9.3** | 122.6 ± 8.2* |
| 1 μM | 158.9 ± 32* | 117 ± 5.6* |
| 10 μM | 137.5 ± 19*** | ND |

*significantly different from the vehicle (p < 0.05)
**significantly different from the vehicle (p < 0.01)
ND — not determined These results demonstrate that 1,6-dimethyl-8β-hydroxymethyl-10α-methoxyergoline (0.1–1 μM) prevents the neuronal death of the co-cultures and increases the number of large motor neurons.

2—Effect of 1,6-dimethyl-8β-hydroxymethyl-10α-methoxyergoline on the neurotrophic activity of the motor neurons which is produced by the spinal astrocytes:

|  | Motor neuron survival in % Dilutions of the astrocytes in the conditioned medium | | |
| --- | --- | --- | --- |
|  | 1:50 | 1:10 | 1:4 |
| Vehicle alone | 36.9 ± 3.2 | 45.4 ± 4.2 | 59.9 ± 8 |
| 1,6-Dimethyl-8β-hydroxymethyl-10α-methoxyergoline | 49.6 ± 5.3** | 74.8 ± 6.3** | 90.6 ± 4.9** |

**significantly different from the vehicle (p < 0.01)

These results demonstrate that 1,6-dimethyl-8β-hydroxymethyl-10α-methoxyergoline stimulates the motor neuron trophic activity which is produced by the spinal astrocyte monolayers.

3—Effect of 1,6-dimethyl-8β-hydroxymethyl-10α-methoxyergoline on co-cultures of astrocyte monolayers and motor neurons

|  | Motor neuron survival in % Concentration of the tested product | | | |
| --- | --- | --- | --- | --- |
|  | 1 μM | 100 nM | 10 nM | 1 nM |
| Vehicle alone | 43.9 ± 4 | | | |
| 1,6-Dimethyl-8β-hydroxymethyl-10α-methoxyergoline | 68.7 ± 8** | 57.4 ± 4** | 48.9 ± 3** | 42.5 ± 4 |

**significantly different from the vehicle (p < 0.01)

These results demonstrate the efficacy of 1,6-dimethyl-8β-hydroxymethyl-10α-methoxyergoline in motor neuron trophic stimulation by the astrocytes.

4—Neurotrophic-like effect of 1,6-dimethyl-8β-hydroxymethyl-10α-methoxyergoline on neuronal death in motor-neuron-enriched cultures and in the absence of trophic factor:

1,6-Dimethyl-8β-hydroxymethyl-10α-methoxy-ergoline increases the survival of trophic factor-deprived motor neurons by 60% (p<0.001), while neuronal arborization and cell morphology remain well preserved.

These results suggest that 1,6-dimethyl-8β-hydroxymethyl-10α-methoxyergoline exerts a neurotrophic effect on this degeneration model, which is induced by depriving cultured motor neurons of trophic factor, and, furthermore, stimulates the ostracise which produce this neurotrophic factor.

The present invention also relates to the use of 1,6-dimethyl-8β-hydroxymethyl-10αa-methoxyergoline for preparing a pharmaceutical which is of use in preventing and/or treating motor neuron diseases, in particular amyotrophic lateral sclerosis, progressive spinal muscular atrophy, infantile muscular atrophy and primary lateral sclerosis.

1,6-Dimethyl-8β-hydroxymethyl-10α-methoxy-ergoline can be prepared using the method described in French Patent No. 2,616,788.

The pharmaceuticals at least comprise 1,6-dimethyl-8β-hydroxymethyl-10α-methoxyergoline, either in the pure state or in the form of a composition in which it is associated with any other pharmaceutically compatible product, which may be inert or physiologically active. The pharmaceuticals according to the invention can in particular be employed by the oral route or by the parenteral route.

It is possible to use tablets, pills, powders (gelatin capsules and tablets), oral lyophilisates (Lyoc$^R$) or granules as solid compositions for oral administration. In these compositions, the active principle is mixed with one or more inert diluents, such as starch, tartaric acid, gum arabic, sodium saccharin, vanillin, cellulose, sucrose, lactose or silica under a current of argon. These compositions can also comprise substances other than diluents, for example one or more lubricants such as magnesium stearate or talc, a dye, a coating (sugar-coated tablets) or a varnish.

It is possible to use pharmaceutically acceptable solutions, suspensions, emulsions, syrups and elixirs, containing inert diluents such as water, ethanol, glycerol, vegetable oils or paraffin oil, as liquid compositions for oral administration. These compositions can comprise substances other than the diluents, for example wetting, sweetening, thickening, aromatizing or stabilizing products.

The sterile compositions for parenteral administration can preferably be aqueous or nonaqueous solutions, suspensions or emulsions. It is possible to employ water, propylene glycol, a polyethylene glycol, vegetable oils, in particular olive oil, injectable organic esters, for example ethyl oleate, or other suitable organic solvents, as solvent or vehicle.

These compositions can also comprise adjuvants, in particular wetting, isotonizing, emulsifying, dispersing and stabilizing agents. Sterilization can be effected in a variety of ways, for example by asepticizing filtration, by incorporating sterilizing agents into the composition, by irradiation or by heating. The compositions can also be prepared in the form of sterile solid compositions which can be dissolved at the time of use in sterile water or any other injectable sterile medium.

FORMULATION EXAMPLES:

Capsule: 10 mg of 1,6-dimethyl-8β-hydroxymethyl-10α-methoxyergoline and, as excipients, talc, lactose and magnesium stearate.

Oral lyophilizate: 10 mg of 1,6-dimethyl-8β-hydroxymethyl-10α-methoxyergoline and, as excipients, tartaric acid, lactose, gum arabic, sodium saccharin and vanillin.

Powder for parenteral use: 10 mg of 1,6-dimethyl-8β-hydroxymethyl-10α-methoxyergoline and, as excipients, tartaric acid and lactose.

The doses depend on the sought-after effect, on the duration of the treatment and on the administration route employed; they are generally between 30 and 200 mg per day by the oral route for an adult, with unit doses ranging from 5 to 50 mg of 1,6-dimethyl-8β-hydroxymethyl-10α-methoxyergoline.

In a general manner, the doctor will determine the appropriate dosage according to the weight and all the other factors which are peculiar to the subject to be treated.

The invention also relates to the method for preventing and/or treating motor neuron diseases, in particular amyotrophic lateral sclerosis, progressive spinal muscular atrophy, infantile muscular atrophy and primary lateral sclerosis, which consists in administering 1,6-dimethyl-8β-hydroxymethyl-10α-methoxyergoline to the patient.

What is claimed is:

1. A method for the treatment or prevention of motor neuron diseases comprising administering to a patient in need thereof an effective amount of 1,6-dimethyl-8β-hydroxymethyl-10α-methoxyergoline or a pharmaceutically acceptable salt thereof, optionally in combination with a pharmaceutically acceptable carrier.

2. The method of claim 1 wherein the motor neuron disease is amyotrophic lateral sclerosis, progressive spinal muscular atrophy, infantile muscular atrophy or primary lateral sclerosis.

3. The method of claim 2 wherein the disease is amyotrophic lateral sclerosis.

4. The method of claim 2 wherein the disease is progressive spinal muscular atrophy.

5. The method of claim 2 wherein the disease is infantile muscular atrophy.

6. The method of claim 2 wherein the disease is primary lateral sclerosis.

* * * * *

UNITED STATES PATENT AND TRADEMARK OFFICE
CERTIFICATE OF CORRECTION

PATENT NO.     : 6,339,095 B2
DATED          : January 15, 2002
INVENTOR(S)    : Michel Dib It is certified that error appears in the above-identified patent and that said Letters Patent is hereby corrected as shown below:

Title page,
Item [30], Foreign Application Priority Data, reads "Nov. 13, 1998 (FR) …………...98 14250" and should read -- Nov. 24, 1998 (FR) …………..98 14792 --.

Column 2,
Line 48, reads "1,6-dimethyl-80β-" and should read -- 1,6-dimethyl-8β- --.
Line 58, reads "medium. he" and should read -- medium. The --.

Column 4,
Line 33, reads "10αa-methoxyergoline" and should read -- 10α-methoxyergoline --.

Column 5,
Lines 30 and 31, reads "-10αa-methoxyergoline." and should read -- -10α-methoxyergoline --.

Signed and Sealed this

Twenty-fourth Day of September, 2002

Attest:

Attesting Officer

JAMES E. ROGAN
*Director of the United States Patent and Trademark Office*